United States Patent [19]

Wright et al.

[11] 4,171,356

[45] Oct. 16, 1979

[54] 2-UNSUBSTITUTED DERIVATIVES OF 4,6-DI-O-(AMINOGLYCOSYL)-1,3-DIAMINOCYCLITOIS, METHODS FOR THEIR USE AS ANTIBACTERIAL AGENTS AND COMPOSITIONS USEFUL THEREFOR

[75] Inventors: John J. Wright, Cedar Grove; Alan K. Mallams, West Orange, both of N.J.

[73] Assignee: Schering Corporation, Kenilworth, N.J.

[21] Appl. No.: 736,640

[22] Filed: Oct. 28, 1976

[51] Int. Cl.$^2$ .................. A61K 31/71; C07H 15/22
[52] U.S. Cl. .................. 424/180; 260/349; 536/10; 536/12; 536/13; 536/17 R
[58] Field of Search .................. 424/180; 536/10, 17

[56] References Cited

U.S. PATENT DOCUMENTS

| 3,920,628 | 11/1975 | Daniels | 536/17 |
| 3,985,727 | 10/1976 | Daniels | 536/17 |

FOREIGN PATENT DOCUMENTS

| 835898 | of 1976 | Belgium | 536/17 |
| 4939 | of 1974 | South Africa | 536/17 |

*Primary Examiner*—Johnnie R. Brown
*Attorney, Agent, or Firm*—Elizabeth A. Bellamy; Mary S. King

[57] ABSTRACT

The preparation of novel 2'-unsubstituted derivatives of 4,6-di-O-(aminoglycosyl)-1,3-diaminocyclitols, useful as antibacterial agents, is described.

14 Claims, No Drawings

2-UNSUBSTITUTED DERIVATIVES OF 4,6-DI-O-(AMINOGLYCOSYL)-1,3-DIAMINOCYCLITOIS, METHODS FOR THEIR USE AS ANTIBACTERIAL AGENTS AND COMPOSITIONS USEFUL THEREFOR

FIELD OF THE INVENTION

This invention relates to novel compositions of matter, to methods for their manufacture and methods for their use as antibacterial agents.

Specifically, this invention relates to novel 2'-unsubstituted derivatives of 4,6di-O-(aminoglycosyl)-1,3-diaminocyclitols useful as antibacterial agents. Further, this invention relates to pharmaceutical compositions comprising said 2'-unsubstituted derivatives, to methods for their manufacture, and to methods for their use in treating bacterial infections.

Particularly, this invention relates to novel 2'-unsubstituted derivatives of 4,6-di-O-(aminoglycosyl)-1,3-diaminocyclitol antibiotics including certain gentamicins, sisomicin, verdamicin, kanamycin A, Antibiotics JI-20B, 66-40B, 66-40D, G-52, Mu-1, Mu-4, and further when the 1,3-diaminocyclitol has a 5 hydroxyl group in the equatorial position, the 5-epi, 5-deoxy, 5-epi-azido-5-deoxy, 5-epi-amino-5-deoxy derivatives thereof and the 1-N-derivatives of the foregoing.

This invention also relates to the process for the preparation of the 2'-unsubstituted-4,6-di-O-(aminoglycosyl)-1,3-diaminocyclitols.

PRIOR ART

Known in the art are 4,6-di-O-(aminoglycosyl)-1,3-diaminocyclitols useful as antibacterial agents, all of which contain a hydroxyl or amino function or derivative thereof at the 2'-position. Antibacterial agents of this group include the gentamicins, sisomicin, verdamicin, the kanamycins and Antibiotics JI-20B, 66-40B, 66-40D, G-52, Mu-1 and Mu-4. Also known in the art are the 1-N-alkyl and 1-N-acyl derivatives of the foregoing (being described in South African Pat. No. 74/4938 which is equivalent to U.S. Pat. No. 4,002,742 for example) and the 5-epi derivatives of the foregoing, as well as the 5-epi-azido-5-deoxy and 5-epi-amino-5-deoxy derivatives (being described in Belgian Pat. No. 835,898 which is equivalent to U.S. Pat. No. 4,000,262) all of which are also antibacterial agents.

By our invention we have discovered methods of preparing 2'-unsubstituted derivatives of the foregoing 4,6-di-O-(aminoglycosyl)-1,3-diaminocyclitols. Further, we have discovered that said 2'-unsubstituted derivatives are also useful antibacterial agents which advantageously are cidal against certain microorganisms which are resistant to the corresponding 2'-substituted-4,6-di-O-(aminoglycosyl)-1,3-diaminocyclitols.

GENERAL DESCRIPTION OF THE INVENTION COMPOSITION-OF-MATTER ASPECT

In its composition-of-matter aspect this invention relates to novel pseudotrisaccharides and their pharmaceutically acceptable acid addition salts. Particularly, this invention relates to 2'-unsubstituted-4,6-di-O-(aminoglycosyl)-1,3-diaminocyclitols wherein the 4-O-aminoglycosyl moiety is defined by one of the following Formulae I and II:

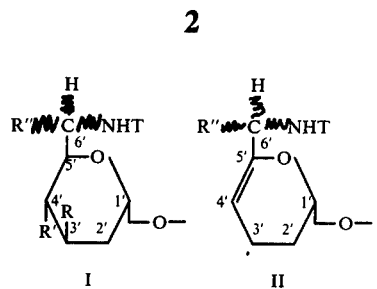

wherein R and R' are each members selected from the group consisting of hydrogen and hydroxy, R" is a member selected from the group consisting of hydrogen and methyl, and T is a member selected from the group consisting of hydrogen, alkyl, hydroxyalkyl and aminoalkyl, said alkyl having up to 4 carbon atoms. Our invention also includes the 1-N-X- derivatives of the foregoing, wherein X is a substituent selected from the group consisting of -CH$_2$-Y and

wherein Y is a member selected from the group consisting of hydrogen, alkyl, alkenyl, cycloalkyl, cycloalkylalkyl, hydroxyalkyl, aminoalkyl, alkylaminoalkyl, aminohydroxyalkyl, and alkylaminohydroxyalkyl, phenyl, benzyl and tolyl, said Y having up to 8 carbon atoms and when said Y is substituted by both amine and hydroxy groups, said groups are on different carbon atoms. Additionally, when the 1,3-diaminocyclitol has a 5-hydroxyl in the equatorial position, our invention embraces the 5-epi, 5-deoxy, 5-epi-azido-5-deoxy and 5-epi-amino-5-deoxy derivatives thereof.

In the Formulae I and II depicted hereinabove, the stereochemical position at the 6' carbon are indicated by wavy lines thus indicating they can be of the R or S configuration; thereby, our invention includes compounds of both stereoconfigurations. Compounds of our invention which are named as 2'-unsubstituted derivatives of known 4,6-di-O-(aminoglycosyl)-1,3-diaminocyclitols thus have the same stereoconfiguration as their 2'-substituted analogs.

Compounds of our invention include 2'-unsubstituted-4,6-di-O-(aminoglycosyl)-1,3-diaminocyclitols wherein the substituents R, R', R" and T in the 4-O-aminoglycosyl moiety of formula I are defined as follows:

(a) R and R' are hydroxy, R" is hydrogen or methyl, and T is hydrogen, e.g. 2'-deoxygentamicin B, 2'-deoxygentamicin B$_1$, 2'-deoxygentamicin A$_3$, 2'-deoxykanamycin A, and 2'-desamino-Antibiotic JI-20B;

(b) R is hydrogen, R' is hydroxy, R" is hydrogen or methyl, and T is hydrogen, e.g. 2', 3'-dideoxygentamicin B, 2',3'-dideoxygentamicin B$_1$, 2', 3'-dideoxygentamicin A$_3$, 2', 3'-dideoxykanamycin A, and 2'-desamino-3'-deoxy-Antibiotic JI-20B;

(c) R and R' are hydrogen, R" and T are hydrogen or methyl, e.g. 2'-desaminogentamicin C$_1$, 2'-desaminogentamicin C$_{1a}$, 2'-desaminogentamicin C$_2$, 2'-desaminogentamicin C$_{2a}$, 2'-desaminogentamicin C$_{2b}$, 2', 3', 4'-trideoxykanamycin A, and 2', 3', 4'-trideoxygentamicin A$_3$.

Other 2'-unsubstituted derivatives of our invention are those wherein the 4-O-aminoglycosyl is defined by formula II, particularly those wherein R" and T are hydrogen or methyl, such as 2'-desaminosisomicin, 2'-desaminoverdamicin, 2'-desamino-Antibiotic 66-40B, 2'-desamino-Antibiotic 66-40D, 2'-desamino-Antibiotic G-52, 2'-desaminoantibiotic Mu-1 and 2'-desaminoantibiotic Mu-4.

It is readily apparent to one skilled in the art that the compounds listed above may have multiple names, e.g. 2'-deoxykanamycin A may also be named as 2'-desaminokanamycin B, 2', 3'-dideoxykanamycin A may also be named as 2'-desaminotobramycin, 2'-deoxygentamicin B may also be named as 2'-desamino-Antibiotic JI-20A, and the like.

Preferred compounds of our invention include those wherein the 6-O-aminoglycosyl is 6-O-garosaminyl and the 1,3-diaminocyclitol is 2-deoxystreptamine.

Included among the substituents contemplated for the moiety T in our novel compounds are straight and branched chain alkyl groups such as methyl, ethyl, n-propyl, isopropyl, n-butyl, isobutyl, tertiary-butyl, and β-methypropyl; hydroxy substituted straight and branched chain alkyl groups such as β-hydroxyethyl, γ-hydroxypropyl, β-hydroxypropyl, δ-hydroxybutyl and β-hydroxy-β-methpropyl; amino substituted straight and branched chain alkyl groups such as β-aminoethyl, β-aminopropyl, γ-aminopropyl, δ-aminobutyl, and β-methyl- γ-aminopropyl.

Included among the substituents contemplated for the moiety Y in our novel compounds are straight and branched chain alkyl groups such as methyl, ethyl, n-propyl, isopropyl, n-butyl, isobutyl, tertiary-butyl, β-methylpropyl, n-pentyl, isopentyl, β-methylbutyl, γ-methylbutyl and β,β-dimethylpropyl: n-hexyl, δ-methylpentyl, β-ethylbutyl, γ-ethylbutyl, n-heptyl, isoheptyl, ε-methylheptyl, β-ethylpentyl, γ-ethylpentyl, δ-ethylpentyl, γ-propylbutyl, n-octyl, iso-octyl, β-ethylhexyl, δ-ethylhexyl, ε-ethylhexyl, β-propylpentyl, γ-propylpentyl; alkenyl groups such as β-propenyl, β-methylpropenyl, β-butenyl, β-methyl-β-butenyl and β-ethyl-β-hexenyl; cycloalkyl groups such as cyclopropyl, cyclobutyl, cyclopentyl and cyclohexyl; cycloalkylalkyl groups such as cyclopropylmethyl, cyclobutylmethyl, cyclopentylmethyl and cyclohexylmethyl; aralkyl groups such as benzyl, o-tolyl, m-tolyl, p-tolyl and phenylethyl; hydroxy substituted straight and branched chain alkyl groups such as ε-hydroxypentyl, β-hydroxy-γ-methylbutyl, β-hydroxy-β-methylpropyl, δ-hydroxybutyl, β-hydroxypropyl, γ-hydroxypropyl, β-hydroxyethyl, ω-hydroxyoctyl; amino substituted straight and branched chain alkyl groups such as ε-aminopentyl, β-aminopropyl, γ-aminopropyl, δ-aminobutyl, β-amino-γ-methylbutyl and ω-aminooctyl; and mono-N- and poly-N-alkylated derivatives thereof such as the N-methyl, N,N-dimethyl, N-ethyl, N,N-diethyl, N-propyl and N,N-dipropyl, e.g. ε-methylaminopentyl, ε-dimethylaminopentyl, β-methylaminopropyl, γ-methylaminopropyl, β-dimethylaminopropyl, γ-dimethylaminopropyl, β-ethylaminopropyl, β-diethylaminopropyl, δ-methylaminobutyl, β-dimethylaminobutyl, β-methylamino-γ-methylbutyl, and ω-methylaminobutyl; γ-aminopropyl, δ-methylaminobutyl, β-methylamino-γ-methylbutyl, and ω-methylaminobutyl; amino and hydroxy disubstituted straight and branched chain alkyl groups such as β-hydroxy-ε-aminopentyl, γ-hydroxy-γ-methyl-δ-aminobutyl, β-hydroxy-δ-aminobutyl, β-hydroxy-γ-aminopropyl, and β-hydroxy-β-methyl-γ-aminopropyl; and mono-N- and poly-N-alkylated derivatives thereof such as β-hydroxy-ε-methylaminopentyl, γ-hydroxy-γ-methyl-δ-methylaminobutyl, β-hydroxy-δ-methylaminobutyl, β-hydroxy-δ-dimethylaminobutyl, β-hydroxy-γ-ethylaminopropyl, β-hydroxy-β-methyl-γ-methylaminopropyl and β-hydroxyγ-dimethylaminopropyl.

Particularly valuable derivatives of the compounds of this invention are the following:

(a) 1-N-X-derivatives, wherein X is $CH_2$-Y, Y being alkyl or aminoalkyl having up to 3 carbon atoms, e.g. 1-N-ethyl-2',3'-dideoxygentamicin B, and 1-N-ethyl-2'-desaminosisomicin;

(b) 1-N-X-derivatives wherein X is a

substituent selected from the group consisting of β-amino-α-hydroxypropionyl, γ-amino-α-hydroxybutyryl and δ-aminoα-hydroxyvaleryl, e.g. 1-N-(β-amino-α-hydroxypropionyl)-2', 3'-dideoxygentamicin B;

(c) 6'-NHT derivatives wherein T is hydrogen, alkyl or aminoalkyl, or hydroxyalkyl, said alkyl having up to 4 carbon atoms; and (d) 5-epi- or 5-deoxy analogs of those 2'-unsubstituted compounds which have a 5-hydroxyl group in the equatorial position, e.g. 5'-epi-2'-desaminosisomicin, and 5'-deoxy-2'-desaminosisomicin.

Also included within the composition-of-matter aspect of this invention are the pharmaceutically acceptable acid addition salts of the 2'-unsubstituted-4,6-di-O-(aminoglycosyl)-1,3-diaminocyclitols described hereinabove, which are made according to known procedures such as by neutralizing the free base with the appropriate acid usually to about pH 5. Included among the pharmaceutically acceptable acid addition salts of this invention are those derived from organic acids such as succinic acid, fumaric acid and maleic acid, or preferably, from inorganic acids such as hydrochloric, sulfuric, phosphoric and hydrobromic. The physical embodiments of the acid addition salts of this invention are characterized by being white solids which are soluble in water, sparingly soluble in most polar organic solvents and insoluble in most non-polar organic solvents.

In general, the microbiological activity of the 2'-unsubstituted derivatives of the 4,6-di-O-(aminoglycosyl)-1,3-diaminocyclitols of this invention and their pharmaceutically acceptable acid addition salts, is similar to that of the parent 4,6-di-O-(aminoglycosyl)-1,3-diaminocyclitols both in vitro and in vivo. Advantageously, however, we have found that removal of the 2'-amino group confers activity against the 2'-N-acetylating strains and in addition, these compounds, as well as those in which the 2'-hydroxyl has been removed, have increased potency against the 3-N-acetylating strains.

The 2'-unsubstituted-4,6-di-O-(aminoglycosyl)-1,3-diaminocyclitols are broad spectrum antibacterials active against both gram-negative and gram-positive strains. Our compounds are particularly active against pathogenic types of gram-negative bacteria such as *E. Coli, Klebsiella, Proteus, Providencia, Pseudomonas, Salmonella*, and *Serratia*; and furthermore are active against gram-positive bacteria such as Staphylococcus, Streptococcus and *B. Subtilis*.

PROCESS ASPECT OF THE INVENTION

The novel pseudotrisaccharides of our invention i.e. the 2'-unsubstituted derivatives of 4,6-di-O-(aminoglycosyl)-1,3-diaminocyclitols, wherein the 4-O-aminoglycosyl moiety is defined in Formulae I and II, may be prepared by the acid catalyzed condensation of a suitably blocked (synonymous with protected) monosaccharide or glycal with the 4-hydroxyl group of a suitably blocked disaccharide to form a blocked pseudotrisaccharide. Utilizing de-blocking techniques well known in the art, the pseudotrisaccharides of our invention are obtained. In our process the monosaccharide is that entity referred to as the 4-O-aminoglycosyl and the disaccharide is that entity containing the 1,3-diaminocyclitol and the 6-0-aminoglycosyl. By "suitably blocked" we mean those groups utilized to protect amino and/or hydroxyl groups during chemical reactions. Our preferred amino protecting groups are benzyloxycarbonyl, ethoxycarbonyl, 2,2,2-trichloroethoxycarbonyl and benzoyl and our preferred hydroxy protecting groups are acetyl and benzoyl.

The choice of the protecting group depends on various factors including whether an amino or hydroxy group is being protected, subsequent reaction conditions, and conditions desired for removal. The choice of the proper protecting group is within the ordinary ability of one skilled in the art.

In general, the preparation of the pseudotrisaccharides of our invention, wherein the 4-O-aminoglycosyl moiety is as defined in Formulae I and II, is effected by certain condensation procedures wherein a blocked or protected disaccharide is reacted with a blocked monosaccharide. Suitably blocked disaccharides useful for producing the pseudotrigaccharides of our invention are represented by the following structural Formulae III–VIII:

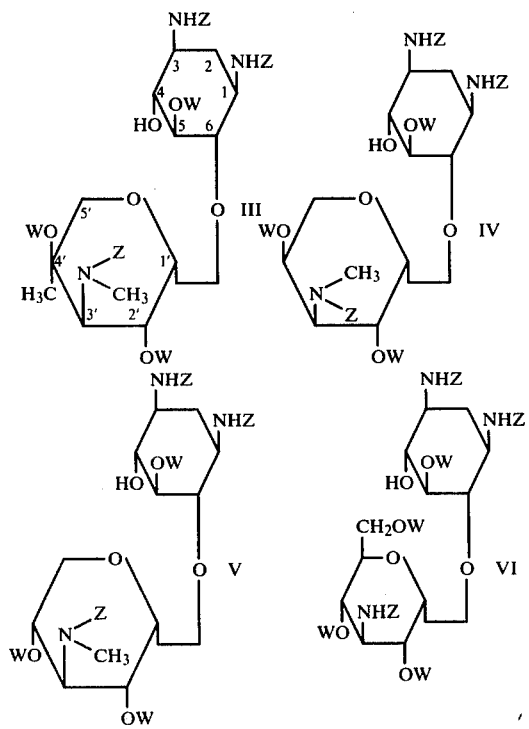

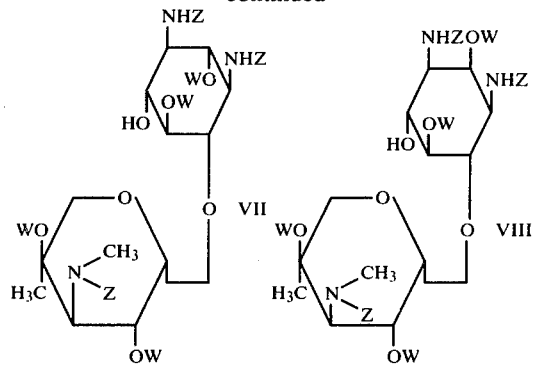

wherein each Z is an amino protecting group and each W is a hydroxy protecting group.

The location of the functional groups in the monosaccharide reactants will predetermine the resultant products of our invention, i.e. whether they are 2'-unsubstituted, 2',3'-di-unsubstituted, 2',3',4'-tri-unsubstituted or 2',4'-di-unsubstituted pseudotrisaccharides. For example, if the blocked monosaccharide of Preparation 7 of the following Formula IX:

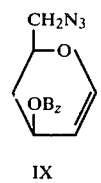

IX is reacted with the blocked disaccharide of Formula III and the resulting blocked pseudotrisaccharide is then de-blocked, one obtains 2',4'-dideoxygentamicin B.

It will be obvious that the 1-N-X, and/or the 5-epi, 5-deoxy, 5-epi-azido-5-deoxy and 5-epi-amino-5-deoxy derivatives of our invention may be obtained by starting with a disaccharide in which the 1,3-diaminocyclitol already contains said 1-N-X or "5" derivatives before condensation with the monosaccharide or, alternatively, by introducing the foregoing groups, as well as a 6'-N-alkyl group, into the corresponding 2'-unsubstituted pseudotrisaccharides of our invention.

Derivatization of the pseudotrisaccharides of our invention may be accomplished by various means. The 1-N-alkyl and 1-N-acyl derivatives of the compounds of our invention may be prepared according to procedures set forth in South African Pat. No. 74/4939. Utilizing one of the methods described therein, reaction of an acid addition salt of a 2'-unsubstituted-4,6-di-O-aminoglycosyl-1,3-diaminocyclitol (e.g. 2'-desaminosisamicin sulfate) in an inert protic solvent containing water with one equivalent of a hydride donor reducing agent (e.g. cyanoborohydride) and at least one equivalent of an aldehyde (e.g. acetaldehyde) yields a 1-N-alkyl-2'-unsubstituted derivative of this invention (e.g. 1-N-ethyl-2'-desaminosisomicin). Similarly, by utilizing one of the methods described in said South African Patent 1-N-acyl derivatives may be prepared. Reaction of an acid addition salt of a 2'-unsubstituted-4,6-di-O-(aminoglycosyl)-1,3-diaminocyclitol (e.g. 2'-desaminosisomicin sulfate) in an inert protic solvent containing water, with one equivalent of an organic or inorganic base (e.g. triethylamine), followed by the addition of a molar excess of an acylating agent (e.g. acetic anhydride)

yields a 1-N-alkanoyl-2'-unsubstituted derivative of this invention (e.g. 1-N-acetyl-2'-desaminosisomicin).

The 5-epi, 5-epi-azido-5-deoxy, 5-epi-amino-5-deoxy derivatives of 4,6-di-O-(aminoglycosyl)-1,3-diaminocyclitols may be prepared according to procedures similar to those described in Belgium Pat. No. 835,898. Thus the 5-epi derivatives of the compounds of this invention may be prepared by the reaction of a 5-O-hydrocarbonsulfonyl-2'-unsubstituted-aminoglycoside (e.g. 5-O-methanesulfonyl -2'-desaminosisomicin) having other hydroxyl and amino groups suitably protected, with dimethylformamide at elevated temperatures, followed by removal of the protecting groups to form the 5-epi-2'-unsubstituted-aminoglycoside (e.g. 5-epi-2'-desaminosisomicin).

The 5-epi-azido-5-deoxy and 5-epi-amino-5-deoxy derivatives of the compounds of this invention may be prepared from a 5-O-hydrocarbonsulfonyl-2'-unsubstituted aminoglycoside (e.g. 5O-methanesulfonyl -2'-desaminosisomicin) having all other amino and hydroxyl groups suitably protected, by reaction thereof with an alkali metal azide in an organic solvent followed by the reaction of the resulting 5-epi-azido-5-deoxy-2'-unsubstituted-protected aminoglycoside (e.g. 5-epi-5-deoxy-protected-2'-desaminosisomicin) with base to remove the protecting groups. Alternatively, reaction of an O and N-protected 5-epi-azido-5-deoxy-2'-unsubstituted derivative with hydrogen in the presence of a catalyst or with an alkali metal in liquid ammonia, and thence cleavage of any remaining hydroxyl or amino protection groups forms a 5-epi-amino-5-deoxy-2'-unsubstituted derivative (e.g. 5-epi-amino-5-deoxy-2'-desaminosisomicin).

The 5-deoxy derivatives of this invention may be prepared according to procedures similar to those described in copending U.S. application Ser. No. 701,387 filed June 30, 1976 (now U.S. Pat. No. 4,053,591). For instance, a 5-O-thioformyl-2'-unsubstituted aminoglycoside (e.g. 5-O-thioformyl-2'-desaminosisomicin) having all amino functions and all primary and secondary hydroxyl groups protected, is reacted with an organotin hydride (preferably tri-n-butylstannane) in an inert protic solvent under an inert atmosphere at temperatures of about 100°C., followed by removal of the protection groups to obtain the 5-deoxy-2'-unsubstituted aminoglycoside (e.g. 5-deoxy-2'-desaminosisomicin).

The 6'-N-alkyl derivatives of this invention may be prepared according to known methods or by procedures similar to those described in co-pending U.S. application Ser. No. 666,715 filed Mar. 15, 1976 (now U.S. Pat. No. 4,044,123). Said 6'-N-alkyl derivatives may be prepared from a 2'-unsubstituted-6'-N-unsubstituted aminoglycoside (e.g. 2'-desaminosisomicin) having protecting groups on all other amino functions, by reaction with an aldehyde or a ketone (e.g. acetaldehyde), followed by reaction in situ of the 6'-N-substituted intermediate thereby formed with a hydride reducing agent, and then removal of any N-protecting groups to obtain the 6'-N-alkyl-2'-unsubstituted aminoglycosides (e.g. 6'-N-ethyl-2'-desaminosisomicin).

The invention described herein above is illustrated in detail herein below in the Preparations and Examples and should not be construed as limiting the scope of our invention.

PREPARATIONS

PREPARATION 1

6-Azidomethyl-5,6-Dihydropyran

Dissolve 4 gm. of 6-hydroxymethyl-5,6-dihydropyran and 10.5 gm. of triethylamine in 100 ml. of anhydrous dichloromethane. Cool the solution and add 5.2 gm. methanesulfonylchloride in 20 ml. of dichloromethane, and stir the reaction for 5 hours. Partition the reaction between water and chloroform, dry the chloroform layer over $MgSO_4$ and then evaporate to a residue in vacuo. Dissolve the residue in 100 ml. of dimethylformamide and add 14 gm. of sodium azide and stir at 50°C. for 60 hours. Filter the reaction mixture, pour the filtrate into ice-water and extract with ether. Evaporate the ether extracts in vacuo. Take up the residue in hexane and wash with water. Dry the organic layer and evaporate in vacuo, and chromatograph the residue on silica gel using 3% acetone in hexane as the eluant to obtain 6-azidomethyl-5,6-dihydropyran, pmr ($CDCl_3$) δ 1.19 (4H, m, ring $CH_2$), 3.55 (2H, d, J= 5.5 Hz, $\underline{CH_2}$-$N_3$), 4.0 (1H, m, H-5), 4.75 (1H, m, H-2), 6.4 (1H, dt, J=1.5, 1.5, 6.5, H-1); ν max (film) 2100, 1650, 1475, 1130 $cm^{-1}$.

PREPARATION 2

6-Azido-6-Deoxy-3,4-Di-O-Benzyl-D-Glucal

Suspend 5.16 gm. of sodium hydride in 50 ml. of ahydrous dimethylformamide. Maintain the temperature at 0°C. and add 12.4 ml. of benzyl chloride, then 4.65 gm. of 6-azido-6-deoxy-D-glucal in 17 ml. of dimethylformamide. Stir for 4 hours and then add 15 ml. of ethanol, after a further 10 minutes, pour the reaction mixture on ice and then extract wth chloroform. Wash the extracts with water, then dry over $MgSO_4$ and then reduce in vacuo. Chromatograph the residue on silica gel using 25% ethyl acetate in benzene as the eluant to obtain 6-azido-6-deoxy-3,4-di-O-benzyl-D-glucal, $[\alpha]^{26}_D$ + 34.3° (EtOH); pmr ($CDCl_3$)δ 3.52 (2H, m, -$CH_2N_3$), 4.6 (4H, m, Ar-$\underline{CH_2}$-), 6.38 (1H, dd, J=1.5, 6-Hz, H-1); ν max ($CHCl_3$) 2100, 1640 $cm^{-1}$.

PREPARATION 3

6-Acetamido-6-Deoxy-3,4-di-O-Benzyl-D-Glucal

Stir a suspension of 760 mg. of lithium aluminum hydride in 50 ml. of tetrahydrofuran and to this add dropwise a solution of 2.98 gm. of 6-azido-6-deoxy-3,4di-O-benzyl-D-glucal in 30 ml. of tetrahyrofuran. Heat the mixture under reflux for 4 hours, cool and add wet ether, filter evaporate the filtrate to a residue. To the residue add 3 ml. of acetic anhydride and 10 ml. of distilled pyridine, stir for 2 hours and remove the solvent, crystallize the residue in chloroform: hexane to obtain 6-acetamido-6-deoxy-3,4-di-O-benzyl-D-glucal $[\alpha]^{26}_D$ −41.8° (EtOH); pmr ($CDCl_3$) δ 1.86 (3H, s, $COCH_3$), 3.65 (2H, m, -$\underline{CH_2}$-N), 4.6 (2H, m, $ArCH_2$), 4.75 (2H, m, Ar-$\underline{CH_2}$), 4.9 (1H, dd, J=3, 6Hz, H-2), 6.45 (1H, dd, J=1.5, 6Hz, H-1); ν max (nujol) 3250, 1640 $cm^{-1}$.

PREPARATION 4

6-C-Methyl-3,4-Di-O-Benzyl-D-Glucal (Mixture of Diastereomeric Alcohols)

Dissolve 1 gm. of 6-azido-6-deoxy-3,4-di-O-benzyl-D-glucal in 250 ml. of dichloromethane and photolyse for 18 hours with a 450 W mercury lamp using a pyrex filter. Evaporate the solution and take up the residue in 50 ml. of dry ether. To this residue add dropwise, with cooling, 10 ml. of 1.3 molar equivalents of ethyl magnesium bromide in ether. Add water and separate out the ether layer. Wash the ether layer with water and dry over MgSO$_4$. Evaporate the ether and chromatograph the residue on silica gel using benzene as the eluant to obtain the mixture of diastereomeric alcohols 6-C-methyl-3,4-di-O-benzyl-D-glucal.

PREPARATION 5

6-Azido-6-Deoxy-6-C-Methyl-3,4-Di-O-Benzyl-D-Glucal (Mixture of Diastereomers)

Dissolve 500 mg. of 6-C-methyl-3,4-di-O-benzyl-D-glucal in 3.5 ml. of pyridine, cool to 0°C. and add 1.8 molar equivalents of p-toluenesulfonylchloride. Let the mixture stand at 4°C. for 18 hours, then add to ice-water. Extract with ether, wash the ether extracts with water and dry over MgSO$_4$. Evaporate off the solvent and dissolve the residue in 5 ml. of dimethylformamide. Add 0.5 gm. of sodium azide and stir for 18 hours at 60°C. Add the reaction mixture to water and extract with ether. Dry the extracts over MgSO$_4$ and then reduce to a residue and chromatograph the resultant residue on silica gel using benzene at the eluant to obtain diastereomeric mixture of 6-azido-6-deoxy-6-C-methyl-3,4-di-O-benzyl-D-glucal.

PREPARATION 6

6-Amino-6-N-Methyl-6-N-Benzyloxycarbonyl-3,4,6-Trideoxy-D-Glucal

Dissolve 5 gm. of 6-azidomethyl-5,6-dihydropyran in 50 ml. of ethanol, add 1 gm. of sodium borohydride and heat at reflux for 24 hours. Remove the solvent in vacuo and extract the residue with chloroform. Wash the chloroform extract with water and dry over MgSO$_4$. Evaporate the chloroform and dissolve the residue comprising 6-aminomethyl-5,6-dihydropyran in 100 ml. of aqueous methanol (1:1). Add 3 gm. of sodium carbonate and 5 gm. of benzylchloroformate and stir the reaction for 2 hours. Add 200 ml. of water and extract with chloroform. Dry the chloroform extracts and then evaporate to a residue. Dissolve the residue comprising 6-benzyloxycarbonylaminomethyl-5,6-dihydropyran in 50 ml. dimethylformamide, add 1 gm. of sodium hydride (50% dispersion) and 0.5 ml. of methyl iodide. Stir the reaction mixture for 2 hours and then destroy the excess methyl iodide with acetic acid. Add water and extract with chloroform, evaporate the chloroform and chromatograph the resulting residue on a silica gel column eluting with 1% methanol in chloroform to obtain 6-amino-6-N-methyl-6-N-benzoyloxycarbonyl-3,4,6-trideoxy-D-glucal.

PREPARATION 7

6-Azido-3-O-Benzyl-4,6-Dideoxy-$\underline{D}$-threo-hex-1-enopyranose

Dissolve 33.2 gm. of 1,2,3,6-tetra-O-acetyl-4-deoxy-β-$\underline{D}$-xylo-hexopyranose in 300 ml. of chloroform (ethanol-free). Add a solution 40 gms. of titanium tetrabromide in 100 ml. of chloroform (ethanol-free) and reflux the mixture for 2 hours. Cool the chloroform solution and wash successively with water, aqueous sodium bicarbonate, water, and then dry the chloroform solution over MgSO$_4$. Evaporate the chloroform to dryness to obtain 2,3,6-tri-O-acetyl-4-deoxy-α-$\underline{D}$-xylo-hexopyranosyl bromide.

Dissolve 33 gm. of the bromide in 300 ml. of aqueous acetic acid (1:1) and add portionwise 60 gm. of zinc at 0°C., then stir for 1.5 hours. Add ethyl acetate and filter the slurry and wash the solids with ethyl acetate. Combine the filtrates and wash successively with water, aqueous sodium bicarbonate, water and then dry over MgSO$_4$. Evpaorate the ethyl acetate solution to a residue and chromatograph on a silica gel column (110 × 2.5 cm) using 20% acetone in hexane as the eluant to obtain 3,6-di-O-acetyl-4-deoxy-$\underline{D}$-threo-hex-1-enopyranose.

Dissolve 18 gm. of the acetate in 400 ml. of concentrated ammonium hydroxide and let stand at 25°C. for 24 hours. Evaporate to dryness to obtain 4-deoxy-$\underline{D}$-threo-hex-1-enopyranose.

Dissolve 10 gm. of the alcohol and 15.4 gm. of tosyl chloride in 100 ml. of dry pyridine and let the solution stand at 25°C. for 17 hours. Add ethanol and evaporate the solution to a residue and then azeotrope with toluene. Chromatograph the residue on a silica gel column (110 × 2.5 cm) using 10% acetone in hexane as the eluant to obtain 4-deoxy-6O-tosyl-$\underline{D}$-threo-hex-1-enopyranose.

Dissolve 15 gm. of the tosyl compound in 300 ml. of dry dimethylformamide. Add 10.6 gm. of sodium azide and stir the mixture for 24 hours at 25°C. Pour the reaction mixture into ether and wash the ether layer with water, dry over MgSO$_4$ and then evaporate to a residue to obtain 6-azido-4,6-dideoxy-$\underline{D}$-threo-hex-1-enopyranose.

Dissolve 7.5 gm. of the azide in 150 ml. of dry dimethylformamide and add 2.5 gm. of sodium hydride. Stir the mixture at 25°C. for 1 hour, then add 10 gm. of benzylbromide and stir the mixture at 25°C. for 6 hours. Add a 20% solution of methanol in ether and filter off the solids and wash with chloroform. Combine the filtrates and pour into water and extract with chloroform and dry over MgSO$_4$. Evaporate the chloroform extract and chromatograph the resultant residue on a silica gel column (110 × 2.5 cm) using 5% acetone in hexane as the eluant to obtain 6-azido-3-O-benzyl-4,6-dideoxy-$\underline{D}$-threo-hex-1-enopyranose.

PREPARATION 8

1,3,3'-tri-N-Benzyloxycarbonyl-1-N-Ethylgaramine

Dissolve 10.47 gm. of 1-N-ethylgaramine in 300 ml. of 60% aqueous methanol. Add 15.9 gm. of sodium carbonate and to the reaction add (dropwise) 25.6 gm. of benzyloxycarbonyl chloride. Stir the reaction mixture for 2.5 hours and then add 9.6 gm. of sodium carbonate and 15.3 gm. of benzyloxycarbonylchloride. Stir the reaction for 3 hours and then pour the solution into water. Exract with chloroform, ash the chloroform extracts with water and dry over MgSO$_4$. Concentrate the chloroform solution to a small volume and add it with stirring to ether-hexane (1:1). Filter the resultant solid to obtain 1,3,3'-tr-N-benzyloxycarbonyl-1-N-ethylgaramine, $[\alpha]^{26}_D$ +76.2°(MeOH); pmr (CDCl$_3$) δ 1.05 (6H, m, -CH$_2$-$\underline{CH_3}$ and C-$\underline{CH_3}$), 3.02 (3H, s N-$\underline{CH_3}$), 5.05 (6H, m, Ar-$\underline{CH_2}$), 7.3 (15H, m, aromatic).

PREPARATION 9

5,2',4'-tri-O-Acetyl-1,3,3'-tri-N-Benzyloxycarbonyl-1-N-Ethyl-garamine

Dissolve 18.0 gm. of 1,3,3'-tri-N-benzyloxycarbonyl-1-N-ethylgaramine in 300 ml. of pyridine. Stir the solution at 0°C. and add, dropwise, 5.8 gm. of trichloroethylchloroformate, then let the reaction stand at room temperature for 18 hours. Then add the solution to ice-water and extract the mixture with ethyl acetate. Wash the ethyl acetate extracts successively with water, dilute HCl, water and then dry the ethyl acetate over MgSO$_4$. Concentrate the ethyl acetate solution and add it, with stirring, to hexane-ether (1:1). Collect the 4-O-trichloroethoxycarbonyl derivative by filtration and dissolve in a mixture of 160 ml. of glacial acetic acid, 83.75 ml. of acetic anhydride and 9.25 ml. of concentrated HCl and heat on a steam bath for 3.5 hours. Cool the solution and pour into ice-water. Extract with ethyl acetate and wash the extracts with water, dilute sodium bicarbonate solution, water and then dry over MgSO$_4$. Evaporate the solvent and dissolve the residue comprising 5,2',4'-tri-O-acetyl-1,3,3'-tri-N-benzyloxycarbonyl-1-N-ethyl-4-trichloroethoxycarbonylgaramine in 700 ml. of 90% acetic acid in water. Add 100 gm. of zinc dust and stir for 5 hours, then add an additional 30 gm. of zinc and stir a further 16 hours. Filter off the unreacted zinc and reduce the filtrate in vacuo. Take up the residue in ethyl acetate, wash with water and dry over MgSO$_4$. Chromatograph on a silica gel column using 1% methanol in chloroform as the eluant to obtain 5,2',4'-tri-O-acetyl-1,3,3'-tri-N-benzyloxycarbonyl-1-N-ethylgaramine, $[\alpha]^{26}_D$ +53.5° (MeOH); pmr (CDCl$_3$) $\delta$ 1.12 (3H, t, J=6.5 Hz, -CH$_2$CH$_3$), 1.34, 1.4 (3H, C-CH$_3$), 2.88 (3H, s, N-CH$_3$), 5.12 (6H, m, Ar-CH$_2$), 7.35 (15H, m, aromatic).

EXAMPLES

Example 1

2'-Unsubstituted-4,6-di-O-(Aminoglycosyl)-1,3-Diaminocyclitols

A. 2'-Deoxygentamicin B

Dissolve 1 gm. of 1,3,3'-tri-N-benzyloxycarbonyl-2'-O-acetylgaramine, 0.7 gm. of 6-acetamido-6-deoxy-3,4di-O-benzyl-D-glucal, and 5 mg. of p-toluenesulphonic acid monohydrate in 10 ml. anhydrous benzene and heat the solution at 50°C. for 5 hours. Cool the solution and wash with dilute aqueous sodium bicarbonate and dry over MgSO$_4$. Concentrate the solution in vacuo to a residue and chromatograph on a silica gel column eluating with 1% methanol in chloroform. Follow the eluates by thin layer chromatography to obtain a mixture containing 1,3,3''-tri-N-benzyloxycarbonyl-3',4'-di-O-benzyl-6'-N-acetyl-2''-O-acetyl-2'-deoxygentamicin B. Concentrate the eluates to a residue and dissolve said residue in 5 ml. of tetrahydrofuran and 50 ml. distilled liquid ammnoia. To the solution add, in small pieces, 0.7 gm. of sodium, after 20 minutes allow the solvent to evaporate. Add 5 ml. water and 0.5 gm. sodium hydroxide to the residue and reflux the resulting solution for 3 hours. Cool the solution and stir with an excess of Amberlite IRC-50 (H⊕) ion exchange resin, filter the resin and wash with water. Elute the resin with 3% aqueous ammonium hydroxide, concentrate the eluates in vacuo and lyophilize. Chromatograph the residue on a silica gel column using the lower phase of a chloroform-methanol-15% ammonium hydroxide (2:1:1) as the eluant. Follow the eluates by thin layer chromatography and combine like eluates containing 2'-deoxygentamicin B. Concentrate the combined eluates, dissolve the residue in water and pass over Amberlite IRA-401S (OH⊖) resin and lyophilize to obtain 2'-deoxygentamicin B, $[\alpha]_D^{26}$ +136.7°(H$_2$O); $\delta$ (D$_2$O) 1.18 (3H, s, C-CH$_3$), 2.57 (3H, s, N-CH$_3$), 5.03 (1H, d, J 4Hz, H 1'') and 5.47 (1H, broad d, J 3.5 Hz, H$_1$); cd (TA Cu) [$\theta$]288 −6,360.

B. Other 2'-Unsubstituted Aminoglycosides

In a manner similar to the foregoing, react the following appropriately blocked glucals and disaccharides, 1. 6-(R)-6-azido-6-deoxy-6-C-methyl-3,4-di-O-benzyl-D-glucal and 5,2',4'-tri-O-acetyl-1,3,3'-tri-N-benzyloxycarbonylgaramine,
2. 6-acetamido-6-deoxy-3,4-di-O-benzyl-D-glucal and O-(3-amino-3-deoxy-3-N-methyl-3-N-benzyloxycarbonyl-2,4-di-O-acetyl-$\beta$-L-arabinopyranosyl)-(1→6)-1,3-di-N-benzyloxycarbonyl-5O-acetyl-2-deoxy-D-streptamine,
3. 6-acetamido-6-deoxy-3,4-di-O-benzyl-D-glucal and O-(3-amino-3-deoxy-3-N-benzyloxycarbonyl-2,4,6-tri-O-acetyl-$\alpha$-D-glucopyranosyl)-(1→6)-1,3-di-N-benzyloxycarbonyl-5-O-acetyl-2-deoxy-D-streptamine,
4. 6-(S)-6-azido-6-deoxy-6-C-methyl-3,4-di-O-benzyl-D-glucal and 5,2',4'-tri-O-acetyl-1,3,3'-tri-N-benzyloxycarbonylgaramine, to obtain respectively, the following 2'-unsubstituted aminoglycosides:

1. 2'-deoxygentamicin B$_1$,
2. 2'-deoxygentamicin A$_3$,
3. 2'-deoxykanamycin A, and
4. 2'-desamino-Antibiotic JI-20B.

EXAMPLE 2

2',3'-di-Unsubstituted -4,6-di-O-(aminoglycosyl)-1,3-Diaminocyclitols

A. 2',3'-Dideoxygentamicin B

Dissolve 19.52 gm. of 5,2',4'-tri-O-acetyl 1,3,3'-tri-N-benzyloxycarbonyl garamine, 7.1 gm. of 6-azido-3,6-dideoxy-4-O-acetyl-D-glucal and 180 mg. of p-toluenesulfonic acid monohydrate in 200 ml. anhydrous benzene. Heat the solution at 45°C. for 5 hours and let it adjust to room temperature overnight. Wash the solution with dilute aqueous sodium bicarbonate solution. Dry the benzene solution over MgSO$_4$ and then concentrate in vacuo to a residue. Chromatograph the residue on a silica gel column eluting with 0.25% methanol in chloroform. Follow the eluates by thin layer chromatography and concentrate the less polar eluates to a residue. Dissolve 5 gm. of the residue in 100 ml. of 20% aqueous dioxane, and hydrogenate for 16 hours at room temperature and 55 psi in the presence of 500 mg. of 10% Pd/C. Filter off the catalyst and evaporate the filtrate to dryness. Heat the residue at reflux in a solution of 3 gms. of potassium hydroxide in 20 ml. distilled water for 18 hours. Cool the solution and stir with Amberlite IRC-50 (H⊕) ion exchange resin, filter the resin and wash with water. Elute the resin with 3% aqueous ammonium hydroxide, concentrate the combined eluates in vacuo and chromatograph the residue on a 50 gm. silica gel column using the lower phase of a chloroform-methanol-15% aqueous ammonium hydroxide (2:1:1) as the eluant. Follow the eluates by thin layer chromatography, combine like eluates containing the desired product and concentrate the combined eluates, dissolve the residue in water and pass over Amberlite IRA-401S (OH⊖) resin and lyophilize to obtain 2',3'- dideoxygentamicin B, $[\alpha]_D^{26} +171°$ (H$_2$O); δ (D$_2$O) 1.15 (3H, s, C-CH$_3$), 2.46 (3H, s, N-CH$_3$), 3.75 (1H, dd, J=4, 11 Hz, H-2''), 3.96 (1H, d, J=$\overline{12.5}$ Hz, H-5'' eq.), 5.02 (1H, d, J=4 Hz, H-1''), and 5.27 ppm (1H, broad, s, W ½=5 Hz, H-1'''); cd (TA Cu) [θ]$_{28}$ −10,100.

B. Other 2',3'-Di-Unsubstituted Aminoglycosides

In a manner similar to the foregoing, react the following appropriately blocked glucals and disaccharides,
1. 6-(R)-6-azido-3,6-dideoxy-6-C-methyl-4-O-benzyl-D-glucal and 5,2',4'-tri-O-acetyl-1,3,3'-tri-N-benzyloxycarbonylgaramine,
2. 6-azido-3,6-dideoxy-4-O-acetyl-D-glucal and O-(3-amino-3-deoxy-3-N-methyl-3-N-benzyloxycarbonyl-2,4'-di-O-acetyl-β-L-arabinopyranosyl)-(1→6)-1,3-di-N-benzyloxycarbonyl-5-O-acetyl-2-deoxy-D-streptamine.
3. 6azido-3,6-dideoxy-4-O-acetyl-D-glucal and O-(3-amino-3-deoxy-3-N-benzyloxycarbonyl-2,4,6-tri-O-acetyl-α-D-glucopyranosyl)-(1→6)-1,3-di-N-benzyloxycarbonyl-5-O-acetyl-2-deoxy-D-streptamine,
4. 6-(S)-6-azido-3,6-dideoxy-6-C-methyl-4-O-benzyl-D-glucal and 5,2',4'-tri-O-acetyl-1,3,3'-tri-N-benzyloxycarbonylgaramine, to obtain, respectively, the following 2',3'-di-substituted aminoglycosides:
1. 2',3'-dideoxygentamicin B$_1$,
2. 2',3'-dideoxygentamicin A$_3$,
3. 2',3'-dideoxykanamycin A, and
4. 2'-desamino-3'-deoxy-Antibiotic JI-20B.

EXAMPLE 3

2',3',4'-Tri-Unsubstituted-4,6-di-O-(Aminoglycosyl)-1,3-Diaminocyclitols

A. 2'-Desaminogentamicin C$_{1a}$

Dissolve 4.33 gm. of 5,2',4'-tri-O-acetyl-1,3,3'-tri-N-benzyloxycarbonylgaramine, 1.54 gm. of 6-azidomethyl-5,6-dihydropyran and 20 mg. of p-toluenesulfonic acid monohydrate in 45 ml. of benzene and heat the solution at 40° C. overnight. Cool the solution and wash with dilute aqueous sodium bicarbonate and dry over MgSO$_4$. Concentrate the solution in vacuo to a residue and chromatograph on a silica gel column using 0.25% methanol in chloroform as the eluant. Follow the eluates by thin layer chromatography, combine the less polar eluates and evaporate. Dissolve the residue in 20 ml. 50% aqueous dioxane, and add 200 mg. of 5% Pd/C and 5 ml. of 0.1 N HCl and hydrogenate at room temperature at 55 psi for 16 hours. Filter, and evaporate the filtrate in vacuo. Dissolve the residue in 4 ml. of 20% aqueous potassium hydroxide and heat at reflux under argon for 16 hours. Cool the solution and adjust the pH to 11 by addition of dilute sulfuric acid. Concentrate the solution to a small volume and add 200 ml. absolute ethanol dropwise while stirring. Filter the resultant mixture and reduce the filtrate to dryness. Dissolve the residue in the lower phase of a chloroform-methanol-10% ammonium hydroxide (2:1:1) solvent system and chromatograph on a silica gel column eluting with the same solvent. Monitor the eluates by thin layer chromatography. Evaporate the less polar eluates containing 2'-desaminogentamicin C$_{1a}$. Dissolve the residue in water and pass over Amberlite IRA-401S (OH$^\ominus$) resin and lyophilize to obtain 2'-desaminogentamicin C$_{1a}$, $[\alpha]_D \approx +166°$ (H$_2$O); δ (D$_2$O) 1.17 (3H, s, C-CH$_3$), 2.48 (3H, s, N-CH$_3$), 3.71 (1H, dd, J=4, 11 Hz, $\overline{\text{H-2''}}$), 4.0 (1H, d, J=12.5 Hz, H-5'' eq.), 5.04 (1H, d, J=4 Hz, H-1'') and 5.30 (1H, broad s, W ½=5Hz, H-1'); cd (TA Cu) [θ]259 −7,760.

B. Other 2',3',4'-Tri-Unsubstituted Aminoglycosides

In a manner similar to the foregoing react the following appropriately blocked glucals and disaccharides,
1. 6-(R)-6-amino-3,4,6-trideoxy-6-C-methyl-6-N-methyl-6-N-benzoyloxycarbonyl-D-glucal and 5,2',4'-tri-O-acetyl-1,3,3'-tri-N-benzyloxycarbonylgaramine,
2. 6-(R)-6-amino-3,4,6-trideoxy-6-C-methyl-6-N-benzyloxycaronyl-D-glucal and 5,2',4'-tri-O-acetyl-1,3,3'-tri-N-benzyloxycarbonylgaramine,
3. 6-(S)-6-amino-3,4,6-trideoxy-6-C-methyl-6N-benzyloxycarbonyl-D-glucal and 5,2',4'-tri-O-acetyl-1,3,3'-tri-N-benzyloxycarbonylgaramine,
4. 6-amino-6-N-methyl-6-N-benzyloxycarbonyl-3,4,6-trideoxy-D-glucal and 5,2',4'-tri-O-acetyl-1,3,3'-tri-N-benzyloxycarbonylgaramine,
5. 6-azidomethyl-5,6-dihydropyran and O-(3-amino-3-deoxy-3-N-benzyloxycarbonyl-2,4,6-tri-O-acetyl-α-D-glucopyranosyl)-(1→6)-1,3-di-N-benzyloxycarbonyl-5-O-acetyl-2-deoxy-D-streptamine,
6. 6-azidomethyl-5,6-dihydropyran and O-(3-amino-3-deoxy-3-N-methyl-3-N-benzyloxycarbonyl-2,4-di-O-acetyl-β-L-arabinopyranosyl)-(1→6)-1,3-di-N-benzyloxycarbonyl-5-O-acetyl-2-deoxy-D-streptamine;

to obtain, respectively, the following 2',3',4'-tri-unsubstituted aminoglycosides:
1. 2'-desaminogentamicin C$_1$,
2. 2'-desaminogentamicin C$_2$,
3. 2'-desaminogentamicin C$_{2a}$,
4. 2'-desaminogentamicin C$_{2b}$,
5. 2',3',4'-trideoxykanamycin A, and
6. 2',3',4'-trideoxygentamicin A$_3$.

EXAMPLE 4

2'-Unsubstituted-4,6-di-O-(Aminoglycosyl)-1,3-diaminocyclitols having 4',5'-Unsaturation A. 2'-Desaminosisomicin Dissolve 410 mg. of 5,2',4'-tri-O-acetyl-1,3,3'-tri-N-benzyloxycarbonylgaramine, 150 mg. of 6-azido-3,6-dideoxy-4-O-acetyl-D-glucal and 3.8 mg. of p-toluenesulfonic acid monohydrate in 35 ml. anhydrous benzene. Heat the solution at 45° C. for 5 hours and let it adjust to room temperature overnight. Wash the benzene solution with dilute aqueous sodium bicarbonate solution, dry the benzene solution over MgSO$_4$ and concentrate in vacuo to a residue. Dissolve the residue in 250 ml. dichloromethane and photolyse with a 450 W Hg lamp for 7 hours. Evaporate the solvent. Repeat the reaction 19 times. Combine the photolysis product of the 19 runs and dissolve in 170 ml. 95% ethanol. Add 6.8 ml. of triethylamine and stir at room temperature for 5 hours. Evaporate the solvent and chromatograph the residue on silica gel using chloroform as the eluant to obtain the 4,5-unsaturated aldehyde.

Dissolve 1.62 gm. of the 4,5-unsaturated aldehyde in 8 ml. of tetrahydrofuran. Add this to a solution of 9.6 gm. ammonium acetate in 45 ml. methanol. Stir for 30 minutes and then add 960 mg. sodium cyanoborohydride and stir at room temperature for 2.5 hours and overnight at 4° C. Add 150 ml. water, extract with 3×100 ml. chloroform, dry the chloroform extracts over MgSO$_4$ and evaporate in vacuo. Dissolve the residue in 15 ml. of dimethylsulphoxide, add 2.6 gm. of potassium hydroxide in 5 ml. of water and stir at room temperature for 48 hours. Adjust the pH of the reaction mixture to 11 by adding dilute HCl, then stir the solution with IRC-50 (H⊕) ion exchange resin. Filter the resin, wash with water and then elute with 6% aqueous ammonium hydroxide. Evaporate the ammoniacal eluate to dryness and chromatograph the residue on silica gel in the lower phase of a chloroform-methanol-7% ammonium hydroxide (2:1:1) system. Follow the eluates by thin layer chromatography, combine like fractions containing 2'-desaminosisomicin, concentrate, pass over Amberlite IRA-401S (OH⊖) resin and lyophilize to obtain 2'-desaminosisomicin, $[\alpha]_D^{26}$ +184.3° (H$_2$O); δ (D$_2$O) 1.18 (3H, s, C-CH$_3$), 2.49 (3H, s, N-CH$_3$), 3.76 (1H, dd, J=4, 11 Hz, $\overline{\text{H-2}}$"), 4.03 (1H, d, J=12.5 Hz, H-5" eq.), 4.92 (1H, m, H-4'), 5.05 (1H, d, J=4 Hz, H-1") and 5.46 (1H, distorted triplet, W ½=6Hz, H-1').

B. Other 2'-Unsubstituted Aminoglycosides having a 4',5'-Unsaturation

In a manner similar to the foregoing, react the following appropriately blocked glucals and disaccharides, 1. 6-(S)-6-azido-3,6-dideoxy-6-C-methyl-4-O-benzyl-D-glucal and 5,2',4'-tri-O-acetyl-1,3,3'-tri-N-benzyloxycarbonylgaramine, 2. 6-azido-3,6-dideoxy-4-O-acetyl-D-glucal and O-(3-amino-3-deoxy-3-N-methyl-3-N-benzyloxycarbonyl-2,4-di-O-acetyl-α-D-xylopyranosyl)-(1→6)-1,3-di-N-benzyloxycarbonyl-5-O-acetyl-2-deoxy-D-streptamine, 3. 6-azido-3,6-dideoxy-4-O-acetyl-D-glucal and O-(3-amino-3-deoxy-3-N-methyl-3-N-benzyloxycarbonyl-2,4-di-O-acetyl-β-L-arabinopyranosyl)-(1→6)-1,3-di-N-benzyloxycarbonyl-5-O-acetyl-2-deoxy-D-streptamine, 4. 6-azido-3,6-dideoxy-4-O-acetyl-D-glucal and 5,2',4'-tri-O-acetyl-1,3,3'-tri-N-benzyloxycarbonylgaramine, (for this preparation methylamine hydrochloride is used instead of ammonium acetate in the above procedure).

5. 6-azido-3,6-dideoxy-4-O-acetyl-D-glucal and O-(3-amino-3-deoxy-3-N-methyl-3-N-benzyloxycarbonyl-4-C-methyl-2,4-di-O-acetyl-β-L-arabinpyranosyl-(1→6)-1,3-di-N-benzoyloxycarbonyl-2,5-di-O-acetyl-D-streptamine, 6. 6-azido-3,6-dideoxy-4-O-acetyl-D-glucal and O-(3-amino-3-deoxy-3-N-methyl-3-N-benzyloxycarbonyl-4-C-methyl-2,4-di-O-acetyl-β-L-arabinopyranosyl)-(1→6)-1,3-di-N-benzyloxycarbonyl-2,5-di-O-acetyl-2-epi-D-streptamine, to obtain, respectively, the following 2'-unsubstituted aminoglycosides having 4',5'-unsaturation:

1. 2'-desaminoverdamicin,
2. 2'-desamino-Antibiotic 66-40B,
3. 2'-desamino-Antibiotic 66-40D,
4. 2'-desamino-Antiobiotic G-52,
5. 2'-desaminomutamicin 1, and
6. 2'-desaminomutamicin 4.

EXAMPLE 5

1-N-X-Derivatives of 2'-Unsubstituted-4,6-di-O-(Aminoglycosyl)-1,3-Diaminocyclitols A. 1-N-Ethyl-2'2',3'-Dideoxygentamicin B Dissolve 2.77 gm. of 4-O-acetyl-6-azido-3,6-dideoxy-D-glucal, 6.14 gm. 5,2',4'-tri-O-acetyl-1,3,3'-tri-N-benzyloxycarbonyl-1-N-ethylgaramine and 50 mg. p-toluenesulphonic acid in 100 ml. anhydrous benzene and stir at 40° C. for 18 hours. Cool the solution and wash with dilute NaHCO$_3$, dry over MgSO$_4$ and concentrate in vacuo. Chromatograph on silica gel in 0.25% methanol in chloroform and follow the eluates by thin layer chromatography. Dissolve the product (2.56 gm.) from the combined less polar fractions in 125 ml. 25% aqueous dioxane, add 10% pd/C and hydrogenate at 56 psi for 16 hours. Filter the reaction mixture and evaporate the filtrate in vacuo to a residue. Heat the residue in 20 ml. 2 N sodium hydroxide at 100° C. for 16 hours under argon. Cool the solution and adjust the pH to 11 with the addition of 1 N H$_2$SO$_4$. Concentrate the solution to a small volume and add 200 ml. absolute ethanol dropwise while stirring. Filter the mixture and reduce the filtrate to dryness. Take up the residue in the lower phase of a chloroform-methanol-10% ammonium hydroxide (2:1:1) solvent system and chromatograph on a silica gel column in the same solvent. Monitor the eluates by thin layer chromatography. Evaporate the combined eluates containing the desired product and dissolve the residue in water, pass over Amberlite IRA 401S (OH⊖) resin and lyophilize to obtain 1-N-ethyl-2',3'-dideoxygentamicin B, $[\alpha]D^{26}$+137.5° (MeOH); δ (D$_2$O) 1.05 (3H, t, J=6.5 Hz, CH$_2$-CH$_3$), 1.19 (3H, s, C-CH$_3$), 2.51 (3H, s, N-CH$_3$), 3.76 (1$\overline{\text{H}}$, dd, J=4, 11 Hz, H-2"), 4.0 (1H, d, J=12.5, H-5"eg.), 4.96 (1H, d, J=4 Hz, H-1") and 5.32 (1H, broad s, W½=6Hz,H$_1$'); cd (TACu) [θ]287−8,300.

B. Other 1-N-X-derivatives of 2',3'-dideoxygentamicin B

In the above Example, by utilizing as starting compound the 1-N-propyl or 1-N- δ-aminobutyl analog of 5,2',4'-tri-O-acetyl-1,3,3'-tri-N-benzyloxycarbonylgaramine, there is obtained the 1N-propyl-2',3'-dideoxygentamicin B and 1-N-(δ-aminobutyl)-2',3'-dideoxygentamicin B, respectively.

C. 1-N-(S-β-amino-αhydroxypropionyl)-2',3'-dideoxygentamicin B

Dissolve 0.75 gm. of 2',3'-dideoxygentamicin B in 70 ml. of aqueous (2.5%) dimethylsulphoxide and to this solution add, at room temperature, 88.8 mg. hydrated cupric diacetate and 111 mg. nickel(II) diacetate. Stir the reaction for 10 minutes and add 132.3 mg. of N-benzyloxycarbonyloxysuccinimide and stir for 2 hours. Then triturate the reaction mixture with dry ether and filter off the solid. Dissolve the solid in 50 ml. methanol-ammonium hydroxide (9:1) and bubble H$_2$S through the solution for 3 minutes. Filter the resulting mixture through celite and stir the filtrate with Amberlite IRA 401S (OH⊖) resin until the solution becomes colorless. Filter, evaporate the filtrate and dissolve the residue in 25 ml. of aqueous (50%) methanol. To this mixture add portion-wise 1.68 gm. of the N-hydroxysuccinimidyl active ester of N-benzyloxycarbonyl-L-isoserine. Stir the reaction for 2 hours and the partition the reaction mixture between water and chloroform. Wash the chloroform layer with water, dry over MgSO$_4$ and then evaporate to dryness. Chromatograph the resultant residue on silica gel eluting with chloroform-methanol-ammonium hydroxide (28% NH$_3$) (12:10:0.5) to obtain 1-N-(S-benzyloxycarbonylamino)-α-hydroxypropionyl)-3,6'-di-N-benzyloxycarbonyl-2',3'-dideoxygentamicin B.

Hydrogenate 0.35 gm. of said compound in 20 ml. of aqueous (30%) dioxane at one atmosphere with 25 mg. of 5% Pd/C. When the hydrogenation is complete filter the reaction and reduce the filtrate to a residue. Chromatograph the residue on silica gel in the lower phase of a chloroform-methanol-ammonium hydroxide (28% NH$_3$) (2:1:1) solvent system. Follow the eluates by thin layer chromatography, combine like eluates containing the desired product. Concentrate the eluates, dissolve the residue in by thin layer chromatography to obtain the product of the process. Concentrate the eluates, dissolve the residue in water and pass over Amberlite IR 401S (OH⁻) resin and lyophilize to obtain 1-N-(S-β-amino-α-hydroxypropionyl)-2',3'-dideoxygentamicin B, [α]+124.5° (EtOH); 67 (D₂O) 1.13 (3H, s, C—CH₃) 2.43 (3H, s, N—CH₃), 2.47 (1H, d, J = 11 Hz, H-3"), 4.05 (1H, d, J = 12.5 Hz, H-5" eq.), 4.10 (1H, t, J = 5Hz, H-2'), 5.05(1H, d, J = 4 Hz, H-1") and 5.28 (1H, broad s, W ½ = 5.0 Hz, H-1').

D. Other 1-N-X-derivatives of 2',3'-dideoxygentamicin B

In the above Example if the N-hydroxysuccinimidyl active ester of S-4-benzyloxycarbonylamino-2-hydroxybutyric acid or S-5-benzyloxycarbonylamino-2-hydroxyvaleric acid is substituted for N-benzyloxycarbonyl-L-isoserine there is obtained respectively 1-N-(S-α-amino-α-hydroxybutyryl)-2',3'-dideoxygentamicin B or 1-N-(S-α-amino-α-hydroxyvaleryl)-2',3'-dideoxygentamicin B.

EXAMPLE 6

5-Deoxy-Derivatives of 2'-Unsubstituted-4,6-di-O-(aminoglycosyl)-1,3-diaminocyclitols A. 5-Deoxy-2'-Desaminosisomicin (1) 1,3,6'-Tri-N-Ethoxycarbonyl-5-O-Thioformyl-2"-O-Benzoyl-4-3",4"-N-O-Carbonyl-2'-desaminosisomicin To a stirred solution of phosgene (ca 4 gms.) in benzene (30 ml.) add dimethylformamide (3 gms.). Stir the resultant suspension for 30 minutes, then evaporate, add dichloromethane (30 ml.) to the resultant residue and cool in an ice bath. To the cooled solution add 1,3,6'-tri-N-ethoxycarbonyl-2"-O-benzoyl-3",4"-N-,O-carbonyl-2'-desaminosisomicin (6.9 gms.) in dichloromethane (70 ml.) and pyridine (7 ml.). Stir the reaction mixture in an ice bath for 15 minutes, then bubble dry hydrogen sulfide gas through the reaction mixture for 5 minutes. Wash the solution with water, then dilute sulfuric acid and finally with sodium bicarbonate. Dry the solution over sodium sulfate, filter and evaporate. Dissolve the resultant residue in methylene chloride and pour onto a silica gel column (100 gms.) Elute first with chloroform, then elute with 2% methanol in chloroform combining like eluates containing the desired compound as determined by thin layer chromatography, evaporate the combined eluates in vacuo, dissolve the resultant residue in chloroform (30 ml.) and add the chloroform solution to hexane (500 ml.) with vigorous stirring. Separate the resultant precipitate by filtration, then dry the precipitate at 60° C. at 1 millimeter pressure to obtain 1,3,6'-tri-N-ethoxycarbonyl-5-O-thioformyl-2"-O-benzoyl-3",4"-N,O-carbonyl-2'-desaminosisomicin.

(2) 1,3,6'-Tri-N-Ethoxycarbonyl-2"-O-Benzoyl-3",4"-N-O-carbonyl-5-deoxy-2'-Desaminosisomicin Dissolve 1,3,6'-tri-N-ethoxycarbonyl-5-O-thioformyl-2"-O-benzoyl-3",4"-N-O-carbonyl-2'-desaminosisomicin (5.0 gms.) and tri-n-butylstannane (3.5 gms.) in dry toluene (90 ml.) and heat at reflux temperature for 15 hours under an atmosphere of argon. Evaporate the reaction mixture in vacuo, then wash the resultant residue twice by decantation with hexane and dissolve in chloroform. Apply the chloroform solution to a column of silica gel (6 × 30 cm.) containing from 2 to 3% calcium hydroxide. Elute the column with chloroform to remove the tin compounds, then develop the column with a 3% ethanol-chloroform solvent mixture, monitoring the fractions by thin layer chromatography (in 5% methanol:chloroform). Combine those fractions containing 1,3,6'-tri-N-ethoxycarbonyl-2"-O-benzoyl-3",4"-N,O-carbonyl-5-deoxy-2'-desaminosisomicin, evaporate the combined fractions and dry the resultant residue at 60° C. in vacuo to obtain 1,3,6'-tri-N-ethoxycarbonyl-2"-O-benzoyl-3",4"-N,O-carbonyl-5-deoxy-2'-desaminosisomicin.

(3) 5-Deoxy-2'-desaminosisomicin

To a solution of 1,3,6'-tri-N-ethoxycarbonyl-2"-O-benzoyl-3",4"-N,O-carbonyl-5-deoxy-2'-desaminosisomicin (2.1 gms.) in dimethylsulfoxide (18 ml.) add potassium hydroxide (4 gms.) in water (6 ml.) and stir under an atmosphere of argon for two days. Add water (50 ml.) to the reaction mixture, stir the solution with IRC-50 (H⊕) resin until all the aminoglycoside has been absorbed onto the resin, pour the resin onto the column, then elute with 2 N ammonium hydroxide. Combine the like eluates containing the desired product as determined by thin layer chromatography, evaporate the combined eluates, and chromatograph the resultant residue on silica gel (50 gms.) eluting with the lower phase of a chloroform:methanol:concentrated ammonium hydroxide (2:1:1) system. Combine the like fractions containing the desired product as determined by thin layer chromatography, evaporate the combined fractions, add water to the resultant residue and pass over a small quantity of IRA-401S (OH⊕) resin. Lyophilize the eluate to obtain 5-deoxy-2'-desaminosisomicin.

B. Other 5-Deoxy Derivatives of 2'-unsubstituted-aminoglycosides

In a manner similar to the foregoing react the appropriately N,O-protected derivatives of the 2'-unsubstituted 4,6-di-O-(aminoglycosyl)-1,3-diaminocylitols of our invention to obtain the corresponding 5-Deoxy-2'-unsubstituted derivatives thereof.

EXAMPLE 7

5-Epi-Derivatives of 2'-unsubstituted-4,6-di-O-(aminoglycosyl)-1,3-diaminocyclitols A. 5-Epi-2'-Desaminosisomicin (1) 1,3,6'-tri-N-Benzyloxycarbonyl-5-O-Methanesulfonyl-2"-O-Benzoyl-3",4"-N,O-Carbonyl-2'-desaminosisomicin Dissolve 2.5 gms. of 1,3,6'-tri-N-benzyloxycarbonyl-2"-O-Benzoyl-3",4"-N,O-Carbonyl-2'-desaminosisomicin in 15 ml. of dry pyridine. Cool the solution to 10° C. and add 4 ml. of methanesulfonyl chloride over a period of 10 minutes, allow the reaction mixture to stand overnight, then concentrate the reaction mixture under vacuum at 25° C. Extract the residue with 150 ml. of acid-free chloroform. Wash the chloroform extracts with water and dry over sodium sulfate. Evaporate the chloroform to give 1,3,6'-tri-N-benzyloxycarbonyl-5-O-methanesulfonyl-2"-O-benzoyl-3",4"-N,O-carbonyl-2'-desaminosisomicin.

(2) 5-Epi-2'-Desaminosisomicin

Add 2 gms. of 1,3,6'-tri-N-benzyloxycarbonyl-5-O-methanesulfonyl-2"-O-benzoyl-3",4"-N-O-carbonyl-2'-desaminosisomicin to 15 ml. of dimethylformamide, heat at reflux for 18 hours and then evaporate the solution to a residue. Dissolve the residue in a mixture of 10 ml. of tetrahydrofuran and 50 ml. of liquid ammonia. Slowly add 2 gms. of sodium to the stirred mixture and continue to stir for 2 hours. Allow the ammonia to evaporate by warming to room temperature overnight. Dissolve the resultant residue in 10 ml. of 5% sodium hydroxide and heat at 100° C. for 4 hours. Cool and pass the solution through IRC-50 (H⊕) resin. Wash the resin well with water and elute the product with 100 ml. of 1N ammonium hydroxide. Concentrate the ammonium hydroxide eluate to a residue comprising 5-epi-2'-desaminosisomicin. Purify the product by chromatography on a silica gel column eluting with the lower phase of a chloroform: methanol:15% ammonium hydroxide (2:1:1) solvent system. Combine the like eluates as determined by thin layer chromatography and lyophilize to a residue to obtain 5-epi-2'-desaminosisomicin.

B. Other 5-epi-derivatives of 2'-unsubstituted aminoglycosides

In a manner similar to the foregoing react the appropriately N,O-protected derivatives of the 2'-unsubstituted-4,6-di-O-(aminoglycosyl)-1,3-diaminocyclitols of our invention to obtain the corresponding 5-epi-2'-unsubstituted derivatives thereof.

EXAMPLE 8

5-Epi-Azido-5-deoxy Derivatives of 2'-Unsubstituted-4,6-di-O-(aminoglycosyl)-1,3-diaminocyclitols A. 5-Epi-Azido-5-deoxy-2'-desaminosisomicin
 (1) 1,3,6'-tri-N-Benzyloxycarbonyl-5-Epi-Azido-5-Deoxy-2"-O-Benzoyl-3",4"-N,O-Carbonyl-2'-Desaminosisomicin Dissolve 2 gm. of the product of Example 7A1 in 15 ml. of dry dimethylformamide. Stir the mixture and add 1.5 gm. of sodiumm azide. Keep the reaction mixture under argon at 120° C. overnight. Concentrate the solution under high vacuum. Extract the residue with 200 ml. of acid-free chloroform. Wash the chloroform extracts with water and dry over sodium sulfate. Evaporate the solvent to give 1,3,6-tri-N-benzyloxycarbonyl-5-epi-azido-5-deoxy-2"-O-benzoyl-3",4"-N,O-carbonyl-2'-desaminosisomicin.

(2) 5-Epi-azido-5-deoxy-2'-desaminosisomicin

Reflux a solution of 1 gm. 1,3,6'-tri-N-benzyloxycarbonyl-5-epi-azido-5-deoxy-2"-O-benzoyl-3",4"-N,O-carbonyl-2'-desaminosisomicin in 25 ml. 1:1 dioxane/water and 25 ml. 10% sodium hydroxide for 24 hours. Evaporate the solution to dryness, dissolve the residue in 10 ml. water and neutralize with acetic acid. Evaporate the solution, take up the residue in 5 ml. water and pass through 20 gm. of an Amberlite IRC-50 (H⊕ form) resin column, wash the column with 200 ml. water and then with 100 ml. 1N ammonium hydroxide. Collect the ammonium hydroxide eluate and evaporate to a residue. Freeze dry the residue, then chromatograph on a 25 gm. silica gel column, eluting with chloroform:methanol:7% ammonium hydroxide (2:1:1) to obtain 5-epi-azido-5-deoxy-2'-desaminosisomicin.

B. Other 5-epi-azido-5-deoxy derivatives of 2'-unsubstituted aminoglycosides

In a manner similar to the foregoing, react the appropriately N,O-protected derivatives of the 2'-unsubstituted 4,6-di-O-(aminoglycosyl)-1,3-diaminocyclitols of our invention to obtain the corresponding 5-epi-azido-5-deoxy-2'-unsubstituted derivatives thereof.

EXAMPLE 9

5-epi-amino-5-Deoxy-derivatives of 2'-unsubstituted-4,6-di-O-(aminoglycosyl)-1,3-diaminocyclitols A. 5-Epi-Amino-5-Deoxy-2'-Desaminosisomicin Dissolve the product of Example 8A1 in a mixture of 10 ml. of tetrahydrofuran and 50 ml. of liquid ammonia. Slowly add 2 gm. of sodium to the stirred mixture and continue to stir at −40° C. for 2 hours. Allow the ammonia to evaporate at room temperature overnight. Dissolve the resultant residue in 25 ml. of water and heat to 100° C. overnight. Cool the solution and absorb on Amberlite IRC-50 (H⊕) resin and elute the product with 500 ml. of 1N ammonium hydroxide. Concentrate the ammonium hydroxide eluate under high vacuum to give an oily product. Chromatograph this material on 50 gm. of silica gel using chloroform:methanol: 15% ammonium hydroxide (2:1:1) to give 5-epi-amino-5-deoxy-2'-desaminosisomicin.

B. Other 5-Epi-Amino-5-deoxy derivatives of 2'-unsubstituted aminoglycosides

In a manner similar to the foregoing, react the appropriately -diaminocyclitols of EXAMPLE N,O-protected derivatives of the 2'-unsubstituted 4,6-di-O-(aminoglycosyl)-1,3-diaminocyclitolsof our invention to obtain the corresponding 5-epi-amino-5-deoxy-2'-unsubstituted derivatives thereof.

EXAPLE 10

Acid Addition Salts

A. Sulfate Salts (Sulfuric acid addition salts)

Dissolve 5 gm. of 2'-deoxygentamicin B in 25 ml. of water and adjust the pH of the solution to 4.5 with 1 N sulfuric acid. Pour into about 300 ml. of methanol with vigorous agitation, continue the agitation for about 10–20 minutes and filter. Wash the precipitate with methanol and dry at about 60° C. in vacuo to obtain the corresponding 2'-deoxygentamicin B sulfate.

In like manner, the sulfate salts of the compounds of Examples 1B, 2A, 2B, 3A, 3B, 4A, 4B, 5A, 5B, 6A, 6B, 7A, 7B, 8A, 8B, 9A and 9B be prepared.

B. Hydrochloride Salts

Dissolve 5 gm. of 2'-deoxygentamicin B in 25 ml. of water. Acidify with 2 N hydrochloric acid to pH 5. Lyophilize to obtain the corresponding 2'-deoxygentamicin B hydrochloride.

In like manner, the hydrochloride salts of the compounds of Examples 1B, 2A, 2B, 3A, 3B, 4A, 4B, 5A, 5B, 6A, 6B, 7A, 7B, 8A, 8B, 9A and 9B.

The present invention includes within its scope pharmaceutical compositions comprising our novel 2'-unsubstituted derivatives of 4,6-di-O-(aminoglycosyl)-1,3-diaminocyclitols with a compatible, pharmaceutically acceptable carrier, or coating. Also included within our invention is the method of eliciting an antibacterial response in a warm-blooded animal having a susceptible bacterial infection which comprises administering to said animal a non-toxic, antibacterially effective amount of a member selected from the group consisting of a 2'-unsubstituted derivative of a 4,6-di-O-(aminoglycosyl)-1,3-diaminocyclitol having antibacterial activity.

As discussed hereinabove, the 2'-unsubstituted derivatives of 4,6-di-O-(aminoglycosyl)-1,3-diaminocyclitols of this invention and the non-toxic pharmaceutically acceptable acid addition salts thereof are broad spectrum antibacterial agents which, advantageously, exhibit activity against organisms, particularly gram-negative organisms. Thus, the compounds of this invention can be used alone, or in combination with other antibiotic agents to prevent the growth, or reduce the number of bacteria in various environments. The activity of the 2'-unsubstituted 4,6-di-O-(aminoglycosyl)-1,3-diaminocyclitols against gram-negative bacteria renders them useful for combating infections caused by gram-negative organisms, e.g. species of *E. coli*, and Pseudomonas. Our compounds, e.g. 2'-deoxygentamicin B and 2'-desaminosisomicin have veterinary applications, particularly in the treatment of mastitis in cattle and Salmonella-induced diarrhea in domestic animals such as the dog and the cat. Our compounds may also be used, for example, to disinfect laboratory glassware, dental and medical equipment contaminated with the gram-positive organism, *Staphylococcus aureus*, or other bacteria.

In general, the dosage administered of the 2'-unsubstituted-4,6-di-O-(aminoglycosyl)-1,3-diaminocyclitols will be dependent upon the age and weight of the animal species being treated, the mode of administration, and the type and severity of bacterial infection being prevented, or reduced.

The 2'-unsubstituted-4,6-di-O-(aminoglycosyl)-1,3-diaminocyclitols and the pharmaceutically acceptable acid addition salts thereof may be administered orally. They may also be applied topically in the form of ointments, both hydrophilic and hydrophobic, in the form of lotions which may be aqueous, non-aqueous, or other emulsion type, or in the form of creams or gells. Pharmaceutical carriers useful in the preparation of such formulations will include, for example, such substances as water, oils, fats, waxes, polyesters, alcohols, polyols and the like.

In general, the topical preparations will contain from about 0.1 to about 3.0 gms. of the compounds of this invention per 100 gms. of ointment, creams or lotion. The topical preparations are usually applied gently to lesions from about 2 to about 5 times a day.

For oral administration the antibacterials of this invention may be compounded in the form of tablets, capsules, elixirs, or the like, or may even be admixed with animal feed. It is in these dosage forms that the antibacterials are most effective for treating bacterial infections of the gastrointestinal tract which infections cause diarrhea. They are also useful for pre- and post-operative gut sterilization.

The antibacterials of this invention may be utilized in liquid form such as solutions, suspensions and the like for otic and opthalmic use and may also be administered parenterally via intramuscular, intravenous, subcutaneous and intrasternal injection. The injectable solution, or suspension will usually be administered at from about 1 mg. to about 15 mgs. of anti-bacterial per kilogram of body weight per day divided into about 2 to about 4 doses. The precise dose depends on the stage and severity of the infection, the susceptibility of the infecting organism to the antibacterial and the individual characteristics of the animal species being treated.

The following formulations are to exemplify some of the dosage forms in which the antibacterial agents of this invention and their derivatives may be employed:

| Tablet | Formulation 1 | | | | | |
|---|---|---|---|---|---|---|
| | 10 mg. Tab. | | 25 mg. Tab. | | 100 mg. Tab. | |
| 2'-Deoxygentamicin B | 10.50* | mg. | 26.25* | mg. | 105.00* | mg. |
| Lactose, impalpable powder | 197.50 | mg. | 171.25 | mg. | 126.00 | mg. |
| Corn starch | 25.00 | mg. | 25.00 | mg. | 35.00 | mg. |
| Polyvinylpyrrolidone | 7.50 | mg. | 7.50 | mg. | 7.50 | mg. |
| Magnesium Stearate | 2.50 | mg. | 2.50 | mg. | 3.50 | mg. |
| | 243.0 | mg. | 232.5 | mg. | 277.0 | mg. |

*5% excess

PROCEDURE

Prepare a slurry consisting of the 2'-deoxygentamicin B, lactose and polyvinylpyrrolidone. Spray dry the slurry. Add corn starch and magnesium stearate. Mix and compress into tablets on a suitable press to the specified weight.

| Formulation 2 | |
|---|---|
| Ointment | |
| 2'-Deoxygentamicin B | 1.0 gm. |
| Methyl paraben USP | 0.5 gm. |
| Propyl paraben USP | 0.1 gm. |
| Petrolatum | to 1000 gm. |

PROCEDURE (1) Melt the petrolatum.
(2) Mix the 2'-deoxygentamicin B, methyl paraben and propyl paraben with about 10% of molten petrolatum and make a slurry. Mill the slurry and add to the balance of the petrolatum. Cool to room temperature with agitation.

We claim:
1. A 2'-unsubstituted derivative of a 4,6-di-O-(aminoglycosyl)-1,3-diaminocyclitol antibacterial agent, wherein the 4-O-aminoglycosyl moiety in said 2'-unsubstituted derivative is defined by one of the following Formulae I and II:

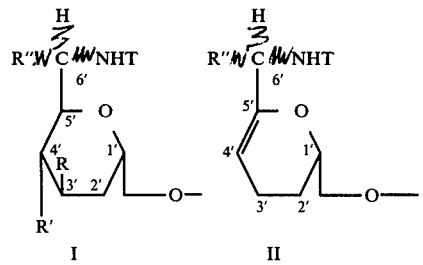

wherein R and R' are each members selected from the group consisting of hydrogen and hydroxy; R" is a member selected from the group consisting of hydrogen and methyl; T is a member selected from the group consisting of hydrogen, alkyl, hydroxyalkyl and aminoalkyl said alkyl having up to 4 carbon atoms;

and when the 1,3-diaminocyclitol has a 5-hydroxyl group in the equatorial position, the 5-epi, 5-deoxy, 5-epi-azido-5-deoxy, 5-epi-amino-5-deoxy derivatives thereof, the 1N-X-derivatives of the foregoing, wherein X is a substituent selected from the group consisting of —CH$_2$—Y and

wherein Y is a member selected from the group consisting of hydrogen, alkyl, alkenyl, cycloalkyl, cycloalkylalkyl, hydroxyalkyl, aminoalkyl, alkylaminoalkyl, aminohydroxyalkyl, alkylaminohydroxyalkyl, phenyl, benzyl and tolyl, said Y having up to 8 carbon atoms and when substituted by both amino and hydroxy groups, said groups are on different carbon atoms;
and the pharmaceutically acceptable acid addition salts thereof.

2. A compound of claim 1 wherein the 6-O-(aminoglycosyl) is garosaminyl and said 1,3-diaminocyclitol is 2-deoxystreptamine.

3. A compound of claim 1, Formula I wherein R and R' are hydroxy, R" is hydrogen or methyl, and T is hydrogen, selected from the group consisting of:
2'-deoxygentamicin B,
2'-deoxygentamicin B$_1$,
2'-deoxygentamicin A$_3$,
2'-deoxykanamycin A, and
2'-desamino-Antibiotic JI-20B.

4. A compound of claim 1, Formula I wherein R and T are hydrogen, R' is hydroxy, and R" is hydrogen or methyl, selected from the group consisting of:
2',3'-dideoxygentamicin B,
2',3'-dideoxygentamicin B$_1$,
2',3'-dideoxygentamicin A$_3$,
2',3'-dideoxykanamycin A, and
2'-desamino-3'-deoxy-Antibiotic JI-20B.

5. A compound of claim 1, Formula I wherein R and R' are hydrogen, and R" and T are hydrogen or methyl, selected from the group consisting of:
2'-desaminogentamicin C$_1$,
2'-desaminogentamicin C$_{1a}$,
2'-desaminogentamicin C$_2$,
2'-desaminogentamicin C$_{2a}$,
2'-desaminogentamicin C$_{2b}$,
2',3',4'-trideoxykanamycin A, and
2',3',4'-trideoxygentamicin A$_3$.

6. A compound of claim 1, Formula II wherein R" and T are hydrogen or methyl, selected from the group consisting of:
2'-desaminosisomicin,
2'-desaminoverdamicin,
2'-desamino-Antibiotic 66-40B,
2'-desamino-Antibiotic 66-40D,
2'-desamino-Antibiotic G-52,
2'-desamino-Antibiotic Mu-1, and
2'-desamino-Antibiotic Mu-4.

7. A 1-N-X-derivative of claim 1 wherein X is —CH$_2$—Y, Y being alkyl or aminoalkyl having up to 3 carbon atoms.

8. A 1-N-X- derivative of claim 1 wherein X is a

substituent selected from the group consisting of β-amino-α-hydroxypropionyl, γ-amino-α-hydroxybutryl, and δ-amino-α-hydroxyvaleryl.

9. A 5-epi or 5-deoxy derivative of claim 1.

10. A compound of claim 7 which is 1-N-ethyl-2',3'-dideoxygentamicin B.

11. A compound of claim 7 which is 1-N-ethyl-2'-desaminosisomicin.

12. A compound of claim 8 which is 1-N-(β-amino-α-hydroxypropionyl)-2',3'-dideoxygentamicin B.

13. The method of eliciting an antibacterial response in a warm-blooded animal having a susceptible bacterial infection which comprises administering to said animal a non-toxic, antibacterially effective amount of a compound of claim 1.

14. A pharmaceutical composition comprising a non-toxic, antibacterially effective amount of a compound of claim 1 together with a non-toxic, pharmaceutically acceptable carrier.

* * * * *

UNITED STATES PATENT AND TRADEMARK OFFICE
CERTIFICATE OF CORRECTION

PATENT NO. : 4,171,356
DATED : October 16, 1979
INVENTOR(S) : John J. Wright et al It is certified that error appears in the above-identified patent and that said Letters Patent are hereby corrected as shown below:

First page, Title, "2-UNSUBSTITUTED" should read ---2'-UNSUB-STITUTED---. Column 1, Title, "2-UNSUBSTITUTED" should read ---2'-UNSUBSTITUTED---; line 44, "74/4938" should read ---74/4939---. Column 3, line 60, "β-dimethylaminobutyl," should read ---δ-dimethylaminobutyl,---. Column 7, line 20, "(e.g. 50-methanesulfonyl" should read ---(e.g. 5-O-methanesulfonyl---; line 25, "(e.g. 5-epi-5-" should read ---(e.g. 5-epi-azido-5---. Column 8, line 22, "3.55" should read ---3.35---. Column 10, line 26, "-6O-tosyl-" should read ---6-O-tosyl---. Column 13, line 5, "$[\Theta]_{28}$" should read ---$[\Theta]_{288}$---; line 66, "$[\alpha]_D^{26}$" should read ---$[\alpha]_D$---. Column 15, line 59, "-2'2',3'-" should read ---2',3'---. Column 16, line 1 "25%" should read ---20%---. Column 17, line 6, "$[\alpha]$+ 124.5°" should read ---$[\alpha]_D^{26}$+ 124.5°---; line 18, "-α-amino-α-" should read ---γ-amino-α---; line 19, "-α-amino-α-" should read ---δ-amino-α---; line 28, "Benzoyl4-3",4"-" should read ---Benzoyl-3",4"---. Column 19, line 41, "1,3,6-" should read ---1,3,6'---. Column 20, line 25, "-priately-diaminocyclitols of Example N,O-" should read ---priately N,O---.

Signed and Sealed this

Eighth Day of July 1980

[SEAL]

Attest:

SIDNEY A. DIAMOND

Attesting Officer   Commissioner of Patents and Trademarks